United States Patent
Drewry et al.

(10) Patent No.: US 8,353,934 B2
(45) Date of Patent: Jan. 15, 2013

(54) CROSSLINK INTERCONNECTION OF BONE ATTACHMENT DEVICES

(75) Inventors: Troy D Drewry, Memphis, TN (US); William B Null, Olive Branch, MS (US); Marc T Paul, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 212 days.

(21) Appl. No.: 12/758,113

(22) Filed: Apr. 12, 2010

(65) Prior Publication Data

US 2010/0198259 A1 Aug. 5, 2010

Related U.S. Application Data

(63) Continuation of application No. 11/401,822, filed on Apr. 10, 2006, now Pat. No. 7,722,648.

(51) Int. Cl.
*A61B 17/70* (2006.01)
*A61B 17/88* (2006.01)

(52) U.S. Cl. ......... 606/250; 606/279; 606/253; 606/252

(58) Field of Classification Search ........... 606/246–279
See application file for complete search history.

(56) References Cited

U.S. PATENT DOCUMENTS

| | | | |
|---|---|---|---|
| 4,957,495 A | 9/1990 | Kluger | |
| 5,084,049 A | 1/1992 | Asher et al. | |
| 5,133,716 A | 7/1992 | Plaza | |
| 5,261,907 A * | 11/1993 | Vignaud et al. | 606/60 |
| 5,522,816 A | 6/1996 | Dinello et al. | |
| 5,624,442 A | 4/1997 | Mellinger et al. | |
| 5,630,816 A | 5/1997 | Kambin | |
| 5,667,507 A | 9/1997 | Corin et al. | |
| 5,707,372 A | 1/1998 | Errico et al. | |
| 5,709,684 A | 1/1998 | Errico et al. | |
| 5,752,955 A | 5/1998 | Errico | |
| 5,885,284 A | 3/1999 | Errico et al. | |
| 5,980,521 A | 11/1999 | Montague et al. | |
| 5,980,523 A | 11/1999 | Jackson | |
| 6,139,548 A | 10/2000 | Errico | |
| 6,217,578 B1 | 4/2001 | Crozet et al. | |
| 6,238,396 B1 | 5/2001 | Lombardo | |
| 6,261,288 B1 | 7/2001 | Jackson | |
| 6,283,967 B1 | 9/2001 | Troxell et al. | |
| 6,432,108 B1 | 8/2002 | Burgess et al. | |
| 6,592,585 B2 | 7/2003 | Lee et al. | |
| 6,699,248 B2 | 3/2004 | Jackson | |

(Continued)

FOREIGN PATENT DOCUMENTS

AU B-16372/92 11/1992

(Continued)

*Primary Examiner* — Eduardo C Robert
*Assistant Examiner* — Jacqueline Johanas

(57) ABSTRACT

An apparatus comprises a pair of bone attachment devices and a crosslink device for a spinal fixation system or other implant arrangement. The bone attachment devices include a head with socket to receive a spinal rod or other elongate element and the crosslink device includes a pair of bridging members each having an end section for connecting with the bone attachment devices. An interconnection device situated between the bridging members receives the bridging members and allows translational and rotational freedom therebetween while being operable to secure the bridging members in position relative to one another. A pair of engaging members are structured to engage the head of the respective bone attachment device and bear against the respective adjacent end of crosslink device to lock the crosslink and the bone attachment device in a rigid construct are also included.

7 Claims, 4 Drawing Sheets

U.S. PATENT DOCUMENTS

| | | | |
|---|---|---|---|
| 6,736,817 B2 | 5/2004 | Troxell et al. | |
| 6,761,721 B2 | 7/2004 | Burgess et al. | |
| 6,872,208 B1 | 3/2005 | McBride et al. | |
| 6,887,241 B1 | 5/2005 | McBride et al. | |
| 6,916,319 B2 | 7/2005 | Munting | |
| 7,722,648 B2* | 5/2010 | Drewry et al. | 606/250 |
| 7,837,714 B2* | 11/2010 | Drewry et al. | 606/250 |
| 8,029,543 B2* | 10/2011 | Young et al. | 606/252 |
| 2002/0007183 A1 | 1/2002 | Lee et al. | |
| 2002/0143327 A1* | 10/2002 | Shluzas | 606/61 |
| 2003/0114853 A1 | 6/2003 | Burgess et al. | |
| 2003/0153914 A1 | 8/2003 | Oribe et al. | |
| 2004/0049188 A1 | 3/2004 | Slivka et al. | |
| 2004/0116928 A1 | 6/2004 | Young et al. | |
| 2004/0133203 A1 | 7/2004 | Young et al. | |
| 2004/0176765 A1 | 9/2004 | Troxell et al. | |
| 2005/0090821 A1 | 4/2005 | Berrevoets et al. | |
| 2005/0101956 A1 | 5/2005 | Simonson | |
| 2005/0177152 A1 | 8/2005 | Baynham et al. | |
| 2005/0216005 A1 | 9/2005 | Howland | |
| 2005/0228326 A1 | 10/2005 | Kalfas et al. | |
| 2006/0064091 A1 | 3/2006 | Ludwig et al. | |
| 2007/0173829 A1* | 7/2007 | Drewry et al. | 606/61 |
| 2007/0270808 A1* | 11/2007 | Drewry et al. | 606/61 |
| 2007/0270809 A1* | 11/2007 | Drewry et al. | 606/61 |

FOREIGN PATENT DOCUMENTS

| | | |
|---|---|---|
| WO | WO 02/076315 | 10/2002 |
| WO | WO 03/030759 | 4/2003 |

* cited by examiner

CROSSLINK INTERCONNECTION OF BONE ATTACHMENT DEVICES

CROSS-REFERENCE TO RELATED APPLICATIONS

This application is a continuation of U.S. patent application Ser. No. 11/401,822 filed on Apr. 10, 2006, which is hereby incorporated herein by reference in its entirety.

BACKGROUND

The present invention relates to a prosthetic device and a manner of using the same, and more particularly, but not exclusively, relates to the interconnection of components to assemble an orthopedic construct for treatment of a spinal deformity.

The use of prosthetic implants to address orthopedic injuries and ailments has become commonplace. In this arena, it is often desired to decrease the invasiveness of the procedures, improve implant integrity, and provide more positive patient outcomes. Some of these implants depend on interconnection between various system components. Unfortunately, current interconnection devices can be limiting in certain applications. Thus, there is a need for additional contributions in this area of technology.

SUMMARY

One form of the present application is a unique prosthesis. Other embodiments include unique methods, systems, devices, instrumentation, and apparatus involving an implantable orthopedic construct.

According to one aspect, there is provided a pair of bone attachment devices designed to engage or attach to bone or a bony structure. The bone attachment devices each include a receiver portion for receiving an elongate spinal stabilization element such as a spinal rod. There also includes a crosslink device which is structured to form a rigid mechanical connection between the two bone attachment devices and is capable of spanning a range of distances and angular orientations separating the two bone attachment devices. The ends of the crosslink device can be secured directly to the receiver portions with the elongate elements in the receiver portions.

In another aspect, a portion of a spinal construct crosslink device includes a first and second member each having an end portion designed to align with a receiver portion of a different one of first and second bone attachment devices. Another portion of the crosslink device includes an interconnection device which is situated between the end portions. The interconnection device includes a passageway to receive the first member and further provides a degree of translational and rotational freedom of movement of the first member to facilitate selection of a desired translational/rotational position before fixing these components together. Another portion of the interconnection device includes a stem which is structured to engage the second member and provides another degree of rotational freedom of movement which further facilitates position selectivity. A fastener is included which is structured to engage the stem and mechanically interconnect the first member and second member together with the interconnection device in a fixed relationship.

Another aspect includes a surgical method for spinal stabilization that may include affixing a first bone attachment device and a second bone attachment device to a corresponding desired skeletal location. In one form, these devices are fixed to the spine. The first and second bone attachment devices each include a receiver portion. A crosslink device has first and second members that are connected by an interconnection device between each end portion. Adjustments may be made to the interconnection device to change the translational position and angular orientation of the first member in relation to the second member. Each end portion of the first and second members can be secured to a respective one of the bone attachment devices by an engaging member engaged to the receiver portion of the bone attachment devices.

Still another aspect includes a bone attachment device with a head defining a socket, a crosslink device, and an elongate spinal stabilization element structured to extend through the socket. The crosslink device includes a first member and a second member each having a connector engagement end portion. The crosslink device further includes means for adjusting the translational and rotational position of the first and second members relative to one another. Also provided are means for fixing one of the first and second connector engagement end portions, the elongate element, and the bone attachment device together in a rigid construct.

Yet another aspect includes a surgical method comprising attaching two bone attachment devices, each having a head with a socket, to a corresponding desired skeletal location; providing two elongate spinal stabilization elements; and positioning each of the two elongate elements in the socket of a different one of the bone attachment devices. The distance between the bone attachment devices may be spanned by providing a crosslink having an interconnection device for adjustably connecting two bridge members and subsequently adjusting the translational and rotational position of the two bridge members relative to one another. The bridge members can be secured to a different one of each of the bone attachment devices by an engaging member engaged to the head of each of the bone attachment devices.

Further embodiments, forms, features, aspects, benefits, objects, and advantages of the present application shall become apparent from the detailed description and figures provided herewith.

DETAILED DESCRIPTION OF SELECTED EMBODIMENTS

Figure 1:
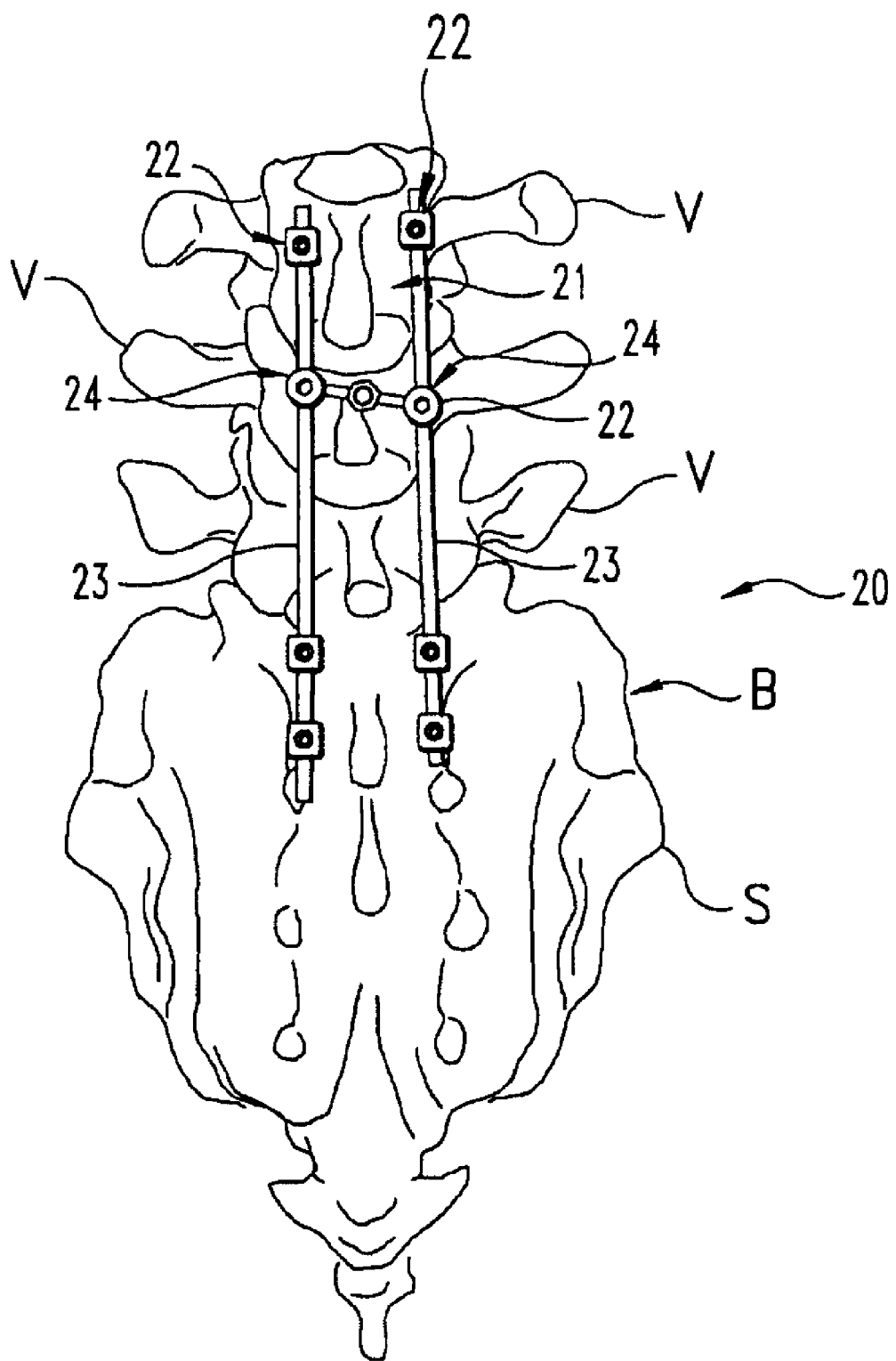
FIG. 1 is a posterior view of a spinal fixation system relative to the spinal column of a patient.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention provides unique orthopedic prosthesis, systems, methods of use and manufacture, devices, instruments, and kits. Incorporated herein by reference in its entirety is U.S. patent application Ser. No. 11/401,732, filed on Apr. 10, 2006, entitled "METHODS AND DEVICES FOR THE INTERCONNECTION OF BONE ATTACHMENT DEVICES" and assigned attorney docket no. MSDI-711/P24819.00.

FIG. 1 illustrates a posterior spinal fixation system 20 of one embodiment located at a desired skeletal location of a patient. More specifically, as depicted in FIG. 1, system 20 is affixed to bones B of the spinal column 21 from a posterior approach. Bones B include the sacrum S and several vertebrae V. System 20 generally includes several bone attachment devices 22 and elongate spinal stabilization elements such as rods 23 structured to selectively interconnect with bone attachment devices 22. In system 20, bone attachment devices 22 are affixed to various locations of the spinal column 21 and interconnected with rods 23. Bone attachment devices 22 may also be interconnected by a crosslink apparatus 24 to provide a stable construct for treating spinal disorders. Posterior fixation system 20 may be used for, but is not limited to, treatment of degenerative spondylolisthesis, fracture, dislocation, scoliosis, kyphosis, spinal tumor, and/or a failed previous fusion.

Figure 2:
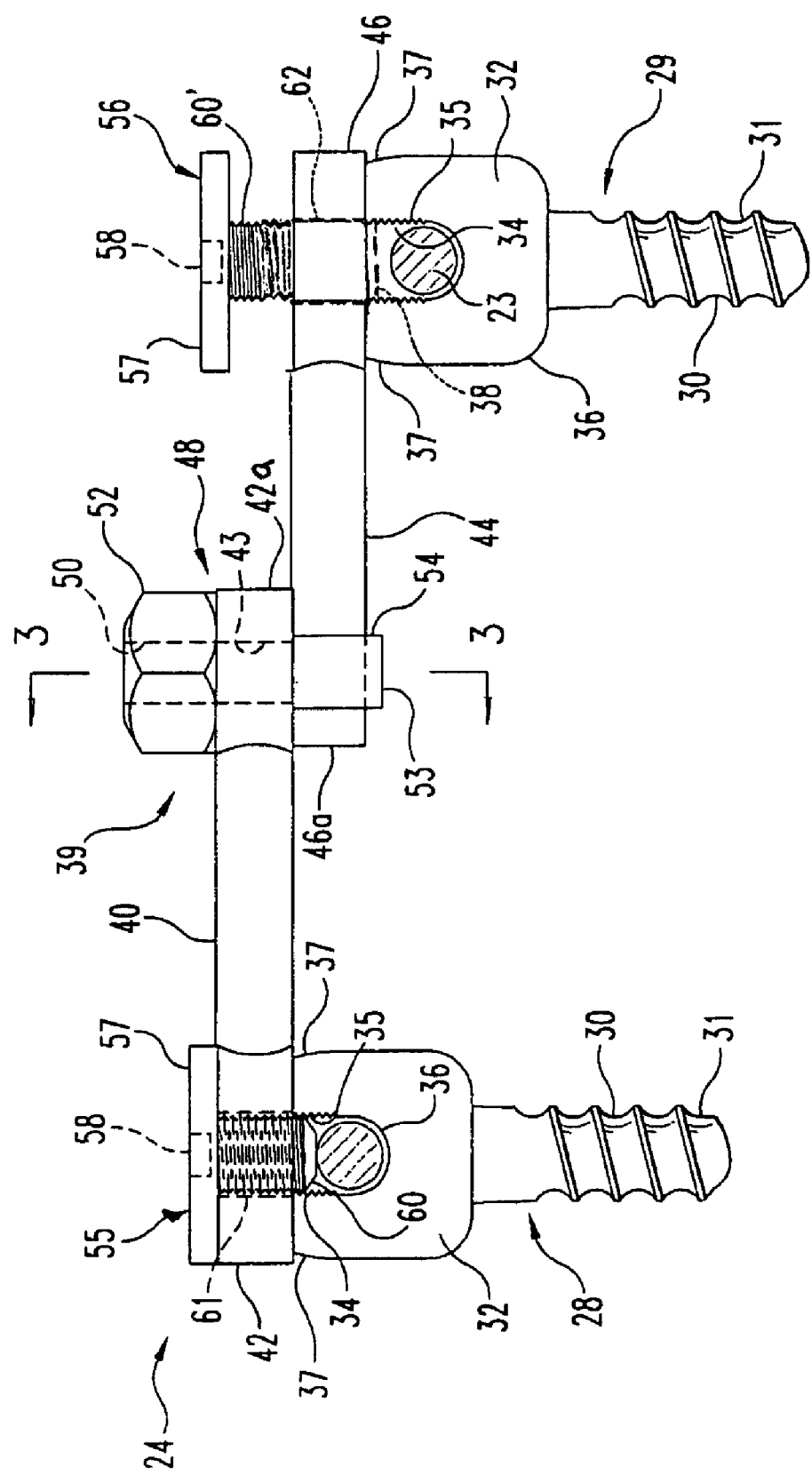
FIG. 2 is a side plan view of a crosslink device included in the spinal fixation device of FIG. 1, with certain hidden features shown in phantom.
Figure 4:
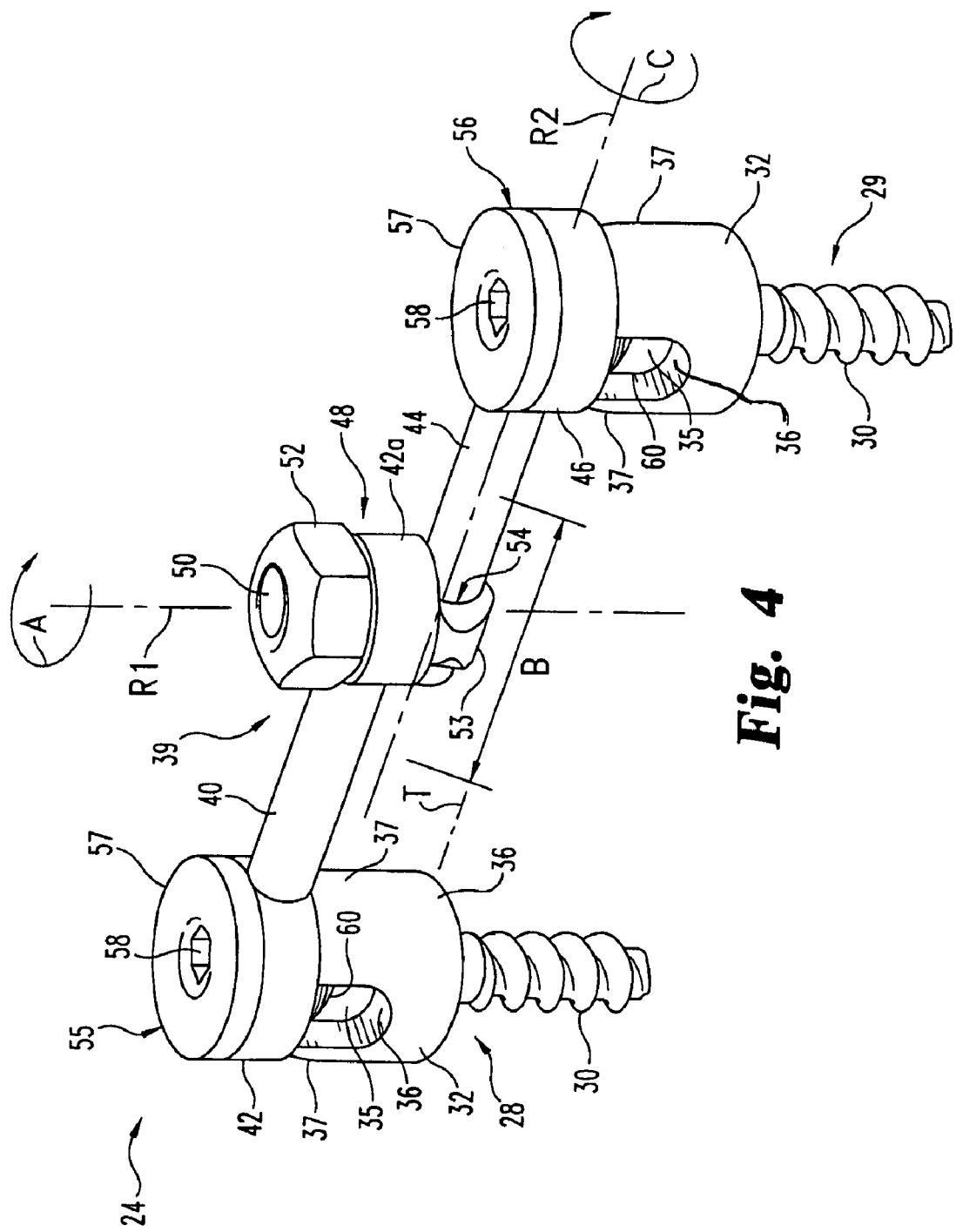
FIG. 4 is a perspective view of the crosslink device of FIG. 2 further illustrating adjustability thereof.

One type of crosslink apparatus 24 is depicted in a side view in FIG. 2 and in a perspective view in FIG. 4; where like reference numerals refer to like features previously described. FIG. 2 further illustrates one of rods 23 of system 20 engaged in a bone attachment device and also FIG. 2 depicts certain hidden features in phantom. FIG. 2 provides a pair of bone attachment devices 22 in the form of a bone screw 28 and a bone screw 29, respectively, that each has an elongated shaft or stem 30 with a helical threaded portion 31. Stem 30 is structured to threadingly engage a passageway prepared in one or more bones or bony structures in a standard manner, and can be provided with cutting flutes or other structure for self-tapping and/or self-drilling capabilities. Stem 30 can also be cannulated to receive a guidewire to facilitate placement and may further include fenestrations or other openings for placement of bone growth material.

Bone screw 28 and bone screw 29 each have a head or a receiver portion 32 defining a socket 35 with internal threading 34. In alternative embodiments not shown, receiver portion 32 has a socket 35 but does not include threading 34, or may include external threading in addition to or alternatively to threading 34. Socket 35 includes a bottom portion 36 and a pair of upright arms 37 forming a channel structured to passively secure rod 23 in socket 35 without additional securing means for those embodiments including rod 23. Bottom portion 36 can be concavely curved and form a portion of a circle to receive the rod in form fitting engagement therein. Other embodiments contemplate that the rod is positioned against a head of a bone screw, or against a cap or crown adjacent a head of a bone screw in receiver portion 32.

In one form bone screw 28 and bone screw 29 are made of medical grade stainless steel but other embodiments may be composed of, but are not limited to, titanium, a titanium alloy or other metallic alloy, and/or a nonmetallic composition. In an alternative embodiment, bone attachment devices 22 may be, but are not limited to, multi-axial, poly-axial, uni-axial, uni-planar bone screws where stem 30 and receiver portion 32 are movable relative to one another. In one movable form, stem 30 and receiver portion 32 are engaged together with a "ball and joint" or swivel type of coupling that permits relative movement therebetween during at least some stages of assembly. In yet another form, bone attachment devices 22 may include one or more hooks to engage an adjacent bony structure such as a pedicle, lamina, spinous process, transverse process, or other bony structure suitably engaged with a spinal hook. For instance, a multi-axial laminar hook form of device 22 can be used in place of screw 28 and/or screw 29. In still other embodiments, device 22 can include a bone attachment structure in the form of a staple, bone plate, interbody fusion device, interbody spacer, spinal anchor, intravertebral fusion device, bone clamp, or other anchor.

In addition, rod 23 may be solid or hollow along some or all of its length and/or may be of homogenous or heterogeneous composition. Rod 23 can be rigid, or be flexible or include one or more flexible portions to permit at least limited spinal motion. Rod 23 may be substituted with any suitable spinal stabilization element positionable along the spinal column, including plates, tethers, wires, cables, cords, inflatable devices, expandable devices, and formed in place devices, for example.

Crosslink apparatus 24 further includes a crosslink device 39 that includes a first bridging member 40 having connector end portion 42 and a second bridging member 44 having connector end portion 46. First and second bridging members 40, 44 can be engaged to one another at ends thereof opposite the respective connecting end portions 42, 46 with an adjustable linking/interconnection device 48. Crosslink device 39 can extend between and interconnect respective ones of the first and second bone attachment devices 22 through which rods 23 are positioned. Crosslink device 39 can include linking/interconnection device 48 that allows change of the angular orientation between and the length of first and second bridging members 40, 44, providing adjustability in the positioning of crosslink device 39 between attachment devices 22 to avoid anatomical structures along the spine.

In one embodiment, connector end portion 42 includes an aperture 61 and connector end portion 46 includes an aperture 62. In alternative embodiments (not shown) connector end portion 42 and/or connector end portion 46 do not include apertures 61, 62 that are completely enclosed. In one such variation, an open collar with a slot is defined by each of end portions 42 and 46 in lieu of the respective enclosed apertures 61 and 62. In another form, the structure of connector end portion 42 and connector end portion 46 have a different means for engaging the respective bone attachment devices 22. Correspondingly, the shape and size of bridging members 40 and 44 can differ from that depicted as desired for a particular application.

For example, the connector end portions 42, 46 can abut against the ends of the respective receiver portions 32, or may include a cavity to at least partially receive the respective receiver portion 32 therein. It should be further understood that connector end portion 42 and 46 may rotate around the respective bone attachment device until finally secured with the respective engaging member 55 and 56. The rotational adjustability of the connector ends 42, 46 with respect to the bone attachment devices further facilitates adjustment in the angular orientation and length of the bridging members 40, 44 relative to one another.

In the embodiment illustrated in FIG. 2 and FIG. 4, apparatus 24 further includes two engaging members 55 and 56 structured to secure crosslink device 39 to bone screws 28 and 29, respectively. Engaging members 55, 56 each include a head 57, and engaging member 55 includes a longitudinal threaded stem 60 opposite head 57 and engaging member 56 includes a longitudinal threaded stem 60' opposite head 57. Head 57 of each of engaging members 55, 56 can include a tool engagement cavity 58. Tool engagement cavity 58 may be, but is not limited to, a hex or alien wrench configuration. In alternative embodiments, tool engagement may be provided by a differently shaped structure for engagement by an appropriate assembly tool or may be absent. Indeed, in one alternative, engaging members 55 and 56 include a frangible, break-away portion which is engaged with a tool to rotate engaging members 55 and 56 into socket 35 until a threshold torque level is reached, at which point the break-away portion fractures, separating from the remaining portions of engaging members 55, 56 at a pre-determined location.

Longitudinal threaded stem 60, 60' of each of engaging members 55, 56 passes through the respective apertures 61 and 62 of corresponding end portions 42 and 46 to engage threading 34 of the respective socket 35. Once threaded therein and tightened, head 57 of each engaging member 55 and 56 bears against the corresponding end portion 42 or 46 to secure the respective bridging members 40 and 44 to the respective receiver portions 32. It should be appreciated that head 57 is sized and shaped to contact end portion 42 or 46 in a bearing relationship including where it forms a material boundary for the corresponding aperture 61 or 62. Accordingly, engaging members 55 and 56 can be utilized to secure crosslink device 39 to first bone screw 28 and second bone screw 29.

FIG. 2 illustrates first bone screw 28 having rod 23 positioned in socket 35 thereof. In various embodiments of this application, socket 35 and rod 23 may differ in size in relation to one another and/or to other components of system 20. Engagement of engaging member 55 in receiver portion 32 causes the end of engaging member 55 to bear against rod 23 and secure rod 23 against the bottom of receiver portion 32 or against other structure in receiver portion 32 to provide a rigid engagement relationship with crosslink device 39 and bone screw 28. In FIG. 2 engaging member 56 is shown not completely engaged with receiver portion 32 of bone screw 29 in order to aid in the depiction of threading 34. However, stem 60' includes a length extending from head 57 such that its distal end stops at a location 38 in receiver portion 32. At location 38 the distal end of stem 60' remains spaced from rod 23 in receiver portion 32. In this configuration, rod 23 is free to axially translate and move relative to bone screw 29 and crosslink device 39 while crosslink device 39 and bone screw 29 are rigidly coupled to one another. It is further contemplated the engaging members 55, 56 may be employed in either or both of bone screws 28, 29 or other bone attachment device 22.

In an alternative embodiment not shown, one or both of the connector end portions 42 and 46 may include a structure that contacts the respective adjacent rod 23 when engaging member 56 with stem 60' is engaged to a bone attachment device 22. Accordingly, when engaging member 56 is tightened, it remains spaced from rod 23 in socket 35, while connecting portion 42, 46 includes a recess to receive receiver portion 32, or includes a structure extending distally therefrom toward rod 23 that contacts and securely engages rod 23 to receiver portion 32 of the bone attachment device.

Engaging members 55, 56 are shown with externally threaded stems. Other embodiments contemplate engaging members 55, 56 with other structures for engaging receiver portion 32, including twist locks, snap fits, interference fits, slide-fits, clamps, expansion fits, and internally threaded stems, for example.

Crosslink device 39 further includes adjustable linking/interconnection device 48 having a stem 50, a fastener 52, and a sleeve 53 defining a passageway 54. Sleeve 53 is positioned opposite stem 50, which extends away therefrom. Bridging member 40 is structured for rotatable engagement with stem 50 and bridging member 44 is structured for translational and rotatable engagement within passageway 54 of sleeve 53. A detailed cross sectional view of interconnection device 48 is provided in FIG. 3 that corresponds to the section line 3-3 presented in FIG. 2.

Bridging member 40 includes end portion 42a opposite connector end portion 42 that defines a passage 43 therethrough. When assembled together as shown in FIGS. 1-4, stem 50 of device 48 extends through passage 43. As in the case of apertures 61 and 62, passage 43 can alternatively be defined as a fork, slot, shim, collar, or blade (just to name a few possibilities) that receives stem 50 instead of the closed opening structure of passage 43. Referring to FIG. 4, bridging member 40 can be moved through a range of rotational positions about axis R1, as represented by the rotational motion arrow A.

Bridging member 44 includes end portion 46a opposite connector end portion 46 that extends through passageway 54 of sleeve 53, and has a range of translational motion along axis T as represented by range segment B. Furthermore, passageway 54 and end portion 46a are sized and shaped to facilitate a range of rotational positions about axis R2 relative to passageway 54 and sleeve 53 as represented by rotational motion arrow C in FIG. 4.

Figure 3:
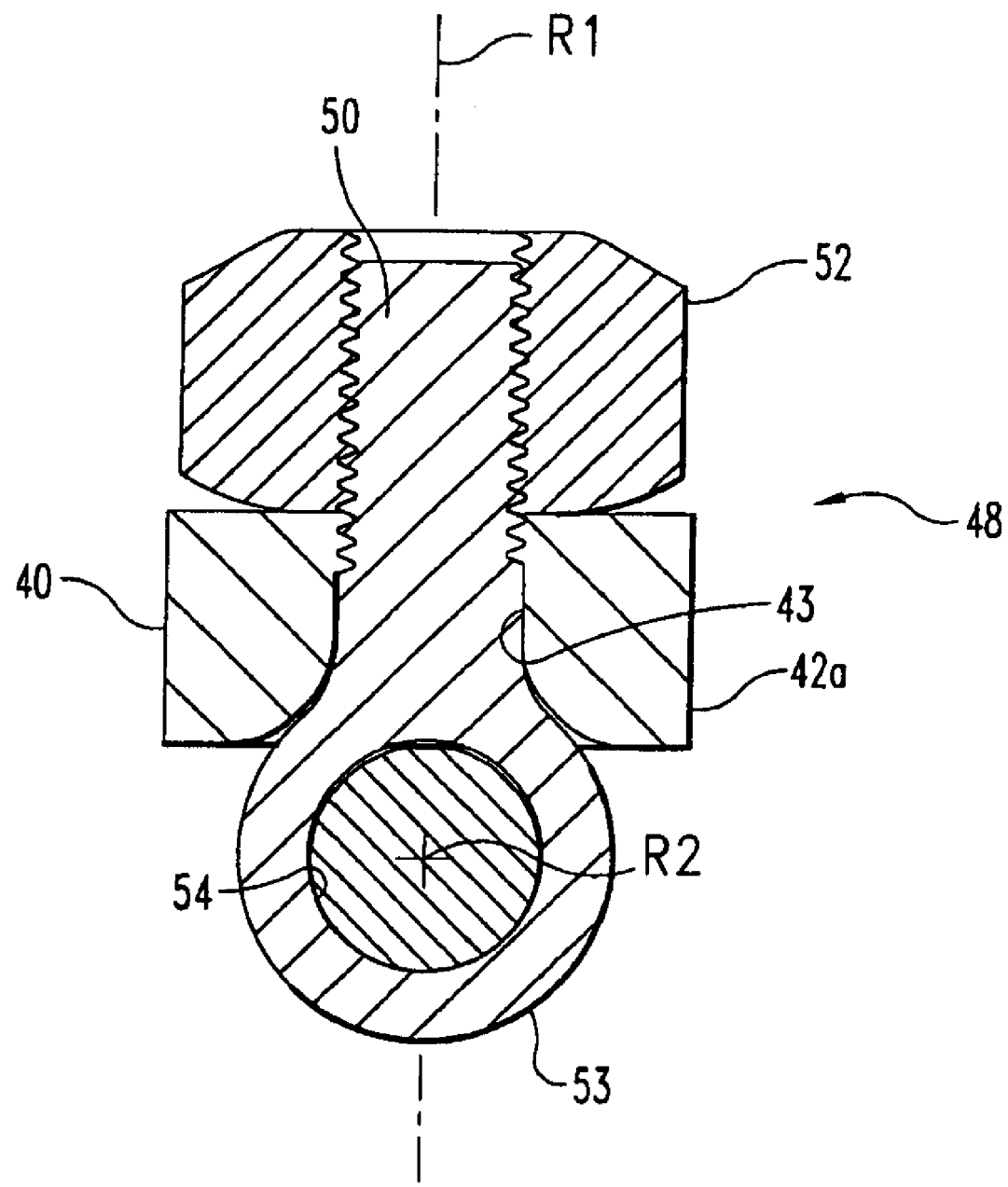
FIG. 3 is a cross sectional view of an interconnection device of the crosslink device shown in FIG. 2.

After extending stem 50 through passage 53 and end portion 46a through passageway 54 and determining selected positioning relative to axes R1, R2, and T, fastener 52 in the form of a nut is threaded on threading of stem 50. As fastener 52 is turned, sleeve 53 brings end portion 46a into contact with end portion 42a, forming a bearing relationship therebetween that resists movement therebetween. Correspondingly, bridging members 40 and 44 become fixed relative to one another as fastener 52 is tightened on stem 50 to bear against a side of end portion 42a opposite the side in contact with end portion 46a. It should be appreciated that before final tightening, refinements can be made in the relative positioning. Once fastener 52 is finally tightened a bridging construct is provided that spans between screws 28 and 29 or other bone attachment devices with a selected rotational configuration relative to axes R1 and R2 (and ranges A and C) and a selected translational configuration relative to axis T along range segment B. Axes R1 and R2 are approximately orthogonal to one another, but such a configuration is note required. In FIG. 3, axis R1 is parallel to the view plane, but axis R2 is perpendicular thereto, being represented by cross hairs. Translation axis T is parallel to axis R2, as best shown in FIG. 4.

In alternative embodiments crosslink device 39 is free from both engaging members 55, 56 and apertures 61, 62. In these embodiments various means for connecting crosslink device 39 with first and second bone attachment devices 22 are included. The means may include, but are not limited to, snap rings, nuts, pins, compression fits, snap fits, clamps, adhesives, and fusions. As the connecting means change the corresponding structure of first connector end 42 and second connector end 46 may also change. In embodiments including rod 23 the manner in which rod 23 is secured to one or both of first bone screw 28 and second bone screw 29 will also change.

The components of crosslink apparatus 24 can be composed of medical grade stainless steel. Other embodiments may be composed of, but are not limited to, titanium, a titanium alloy or other metallic alloy, and/or a nonmetallic composition.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. An apparatus, comprising:
   two attachment devices each including a receiver portion to receive an elongate element therethrough;
   a crosslink device structured to interconnect two attachment devices and adjustably span a distance separating the two attachment devices, the crosslink device including:
   a first member defining a first end portion to align with the receiver portion of a first one of the two attachment devices;
   a second member defining a second end portion to align with the receiver portion of a second one of the two attachment devices;
   an interconnection device positioned between the first end portion and the second end portion to interconnect the first member and the second member together, the interconnection device including:
   a connector body defining a passageway to receive the first member with an adjustable range of translational and first rotational positions relative to the passageway and a stem to engage the second member with an adjustable range of second rotational positions relative to the stem;
   a fastener structured to fix the first member in the passageway at one of the translational positions and one of the first rotational positions and to fix the second member relative to the stem at one of the second rotational positions when engaged to the stem; and
   two engaging members, a first one of the engaging members being structured to engage the first end portion and the receiver portion of the first one of the attachment devices when the first end portion is aligned with the first one of the attachment devices to secure the first member thereto, and a second one of the engaging members being structured to engage the second end portion and the receiver portion of the second one of the attachment devices when the second end portion is aligned with the second one of the attachment devices to secure the second member thereto,
   wherein at least one of the engaging members engages the respective first and second end portion when the engaging member is engaged to the receiver portion and positions the respective first or second end portion against the elongate element extending through the receiver portion to secure the elongate element in position in the receiver portion,
   wherein at least one of the attachment devices is a bone screw and the receiver portion thereof forms a proximal head of the bone screw, the receiver portion including an internal threading and the engaging member engaging the receiver portion includes a threaded stem threadingly engaging the internal threading along the receiver portion.

2. The apparatus of claim 1 wherein the receiver portion is pivotal and rotatable relative to the bone screw.

3. The apparatus of claim 1 wherein the first end portion of the first member and the second end portion of the second member each includes an aperture extending therethrough that aligns with a socket extending into the receiver portion aligned therewith, and the engaging members extend through the respective aperture and into the socket of the receiver portion to threadingly engage the receiver portion.

4. The apparatus of claim 3 wherein the two engaging members each include a longitudinal threaded stem opposite a head, the head of the first engaging member being sized to bear against a boundary defining the aperture through the first end portion when the threaded stem of the first engaging member extends through the aperture in the first end portion, and the head of the second engaging member being sized to bear against a boundary defining the aperture through the second end portion when the threaded stem of the second engaging member extends through the aperture in the second end portion.

5. The apparatus of claim 1 wherein the first end portion of the first member and the second end portion of the second member adjustably attach to the two attachment devices over a range of angular orientations of the respective first and second member relative to the respective attachment device.

6. A method of using a multi-axial crosslink device comprising:
   affixing a first attachment device and a second attachment device each to a corresponding desired location;
   providing a crosslink device including a first member with a first end portion and a second member with a second end portion, the first member and the second member being interconnected between the first end portion and the second end portion by an adjustable interconnection device;
   adjusting the crosslink device with the interconnection device to change translational position of the first member relative to the second member;
   adjusting the crosslink device with the interconnection device to change an angular orientation between the first and second members;
   engaging a first elongate element within a receiving portion of the first attachment device;
   engaging a second elongate element within a receiving portion of the second attachment device;
   securing the first end portion to the first attachment device by engaging the first end portion with an engaging member of the first attachment device thus engaging the first end portion against the first elongate element and securing the first elongate element within the first attachment device, wherein at least one of the attachment devices is a bone screw and the receiving portion thereof forms a proximal head of the bone screw, the receiving portion including an internal threading and the engaging member engaging the receiving portion includes a threaded stem threadingly engaging the internal threading along the receiving portion; and securing the second end portion to the second attachment device by engaging the second end portion with a second engaging member of the second attachment device thus engaging the second end portion against the second elongate element and securing the second elongate element within the second attachment device.

7. The method of claim 6 wherein the first and second attachment devices are each multi-axial bone screws with the receiver portion pivotally and rotationally attached to a bone screw portion.

* * * * *